United States Patent
Durzinsky et al.

(10) Patent No.: US 11,103,198 B2
(45) Date of Patent: Aug. 31, 2021

(54) PROJECTION OF OBJECTS IN CT X-RAY IMAGES

(71) Applicant: Smiths Detection Germany GmbH, Wiesbaden (DE)

(72) Inventors: Markus Durzinsky, Magdeburg (DE); Marc Andreas Mörig, Magdeburg (DE); Sebastian König, Wiesbaden (DE)

(73) Assignee: SMITHS DETECTION GERMANY GMBH, Wiesbaden (DE)

( * ) Notice: Subject to any disclaimer, the term of this patent is extended or adjusted under 35 U.S.C. 154(b) by 60 days.

(21) Appl. No.: 16/484,348

(22) PCT Filed: Feb. 5, 2018

(86) PCT No.: PCT/EP2018/052806
§ 371 (c)(1),
(2) Date: Aug. 7, 2019

(87) PCT Pub. No.: WO2018/146047
PCT Pub. Date: Aug. 16, 2018

(65) Prior Publication Data
US 2020/0000417 A1    Jan. 2, 2020

(30) Foreign Application Priority Data
Feb. 8, 2017   (DE) .......................... 102017102441.7

(51) Int. Cl.
*A61B 6/03*       (2006.01)
*G06T 11/00*     (2006.01)
*A61B 6/00*       (2006.01)

(52) U.S. Cl.
CPC ............ *A61B 6/032* (2013.01); *G06T 11/006* (2013.01); *G06T 11/008* (2013.01); *A61B 6/466* (2013.01); *G06T 11/005* (2013.01); *G06T 2207/10081* (2013.01)

(58) Field of Classification Search
None
See application file for complete search history.

(56) References Cited

U.S. PATENT DOCUMENTS 10,697,903 B2 *   6/2020   Li .......................... G06T 17/00
2014/0161333 A1   6/2014   Litvin et al.
(Continued)

FOREIGN PATENT DOCUMENTS

DE    102014109214 A1    1/2016

OTHER PUBLICATIONS

Translation of International Preliminary Report on Patentability for PCT/EP2018/052806, dated Aug. 13, 2019, 7 Pages.
(Continued)

*Primary Examiner* — Hoon K Song
(74) *Attorney, Agent, or Firm* — Armstrong Teasdale LLP

(57) ABSTRACT

A production method for test X-ray includes preparation (S10) of first CT data (B) of an inspection object, second CT data (BM) for metal portions of the inspection object, and third CT data (TM) for metal portions of a target object, transformation (S20) of the first, second, and third CT data (B, BM, TM) from the image space (BR) into corresponding first sinogram data (SB), second sinogram data (SBM), and third sinogram data (STM) in the radon space (RR), calculation (S30, S40) of the artifact sinogram data (SA), back-transformation (S50) of the artifact sinogram data (SA) from the radon space (RR) into the image space (BR) in CT artifact data (A) for the artifacts that are to be inserted, and insertion of the CT artifact data (A) into the first CT data (B).

20 Claims, 5 Drawing Sheets

(56) References Cited

U.S. PATENT DOCUMENTS

2015/0325010 A1* 11/2015 Bedford ................. G01V 5/005
378/19
2019/0374187 A1* 12/2019 Manhart ............... G06T 3/4007

OTHER PUBLICATIONS

Koehler, T. [et al.]: A New Method for Metal Artifact Reduction in CT. In: Proceedings of the Second International Conference on Image Formation in X-ray Computed Tomography, 2012. https://repository.tudelft.nl/assets/uuid:22d5815d-dcfe-48df-93a4-9d1c4e8e85fc/MS-33.229.pdf [Accessed Dec. 15, 2017].

Megherbi, N. [et al.]: Fully Automatic 3D Threat Image Projection: Application to Densely Cluttered 3D Computed Tomography Baggage Images. In: Proceedings of the 3rd International Conference on Image Processing Theory, Tools, and Applications (IPTA), 2012. DOI: 10.1109/IPTA.2012.6469523.

Najla Megherbi et al. "Radon transform based automatic metal artefacts generation for 3D threat image projection". Bd. 8901, 16. Oct. 16, 2013, Seite 8901B, XP055224962, DOI: 10.1117/12.2028506. ISBN: 978-1-62841-730-2.

German Search Report in DE Application No. 102017102441.7, dated Aug. 2, 2017, 2 pages.

Written Opinion for PCT/EP2018/052806, dated Apr. 5, 2018. 8 Pages.

International Search report for PCT/EP2018/052806, dated Apr. 5, 2018, 5 Pages.

* cited by examiner

PROJECTION OF OBJECTS IN CT X-RAY IMAGES

CROSS REFERENCE TO RELATED APPLICATIONS

This patent application is a National Stage Entry of PCT/EP2018/052806 filed on Feb. 5, 2018, which claims priority to DE Application No. 10 2017 102 441.7 filed on Feb. 8, 2017, the disclosures of which are hereby incorporated by reference herein in their entirety as part of the present application.

FIELD OF DISCLOSURE

The present disclosure relates generally to test X-ray images of inspection objects, which images are produced for example for X-ray inspection units at security checkpoints in airports, wherein an object has been inserted into a test-X-ray image. The present disclosure particularly relates to the production of test X-ray images based on three-dimensional X-ray images of an inspection object produced by means of computed tomography or two-dimensional X-ray images derived therefrom and in this connection, particularly the aspect of producing realistic and plausible metal artifacts, which can be attributed to metal parts contained in the inspection object and metal portions of the object that is to be inserted as well as their reciprocal influences.

BACKGROUND OF THE PRESENT DISCLOSURE

The insertion of a threat object into an X-ray image is known as a "threat image projection" (TIP), as described, for example, by V. Cutler et al. in "Use of Threat Image Projection (TIP) to Enhance Security Performance," 43rd International Carnahan Conference on Security Technology, 5-8 Oct. 2009, pp. 46-51, DOI: 10.1109/CCST.2009.5335565. An X-ray image of real luggage item into which a fictitious threat object has been inserted as though the fictitious threat object were actually present in the real luggage item is referred to as a "fictitious threat image" (FTI).

DE 10 2014 109 214 A1, U.S. Pat. Nos. 6,899,540 B1, and 5,243,693 A give examples of computer systems for training and testing operators of X-ray inspection units for luggage screening.

The known TIP functions essentially relate to 2D test X-ray images of the kind that are customarily produced by X-ray inspection units, which function based on the same principle as a line scanner, in which an inspection object is radiographed line-by-line using X-rays and, based on intensity values of the X-rays after passing through the inspection object, associated lines of a 2D X-ray image are produced.

In the meantime, X-ray inspection units, which function based on the principle of computed tomography (CT), are also used for nondestructive inspection of inspection objects. EP 1 585 995 A1, for example, discloses a corresponding inspection system and inspection method for luggage.

CT X-ray images of inspection objects that contain metal parts usually exhibit so-called metal artifacts. Threat objects such as weapons or explosive devices usually contain metal, e.g. metal components, or consist predominantly or entirely of metal. Correspondingly, a CT FTI must have realistic and plausible metal artifacts, which would be caused by metal objects possibly already present in the inspection object and metal contained in the fictitious threat object. Otherwise, the CT FTI is recognized as an FTI due to unrealistic or implausible metal artifacts.

The imaging in the CT is in principle based on radon data that are detected in a detector, i.e. the detected intensity and direction of an X-ray beam associated with a detector. Every X-ray beam is attenuated as it passes through an inspection object and the materials contained within the beam path. In the computer-aided image reconstruction, for each volume element (voxel) of an inspection object, the attenuation coefficient can be determined as a material property. Based on these attenuation data that exist for all voxels, it is possible to generate a corresponding 3D X-ray image and/or 2D sectional views.

Metal objects have a very high attenuation coefficient so that starting from a particular metal thickness, virtually total absorption can occur because the useful signal detected at the detector then lies below the noise threshold, for example, and can no longer be differentiated. At sharp edges between a metal object and its surroundings, the change in the attenuation coefficients can assume particularly high values. If a combined detector element detects X-rays at such transitions, then an averaging of the detected intensities occurs, with the resulting intensity value being allocated to the respective detector element. Since the logarithm of a linear averaging does not correspond to the sum of the logarithms, this results in an average attenuation coefficient that does not match the average intensities of the detected X-rays. Image artifacts attributable to this are referred to as the partial volume effect. Moreover, the spectrum of an X-ray tube is not monochromatic. The radiation absorption of the materials through which the X-ray passes is energy-dependent. X-rays with low energy are more heavily absorbed than X-rays with high energy. This leads to an increase in the average energy of the overall spectrum. This occurs in all materials, but more intensely in metals. Image artifacts attributable to this are referred to as hardening artifacts.

The above-described effects result in discrepancies in the radon data detected by directing radiation through the inspection object. Since the known image reconstruction by means of filtered back-projection assumes ideal conditions, the detected radon data in the reconstruction are "smeared" over the image region. The effects attributable to metal in the inspection object therefore exert an effect on the entire image. In other words, metal artifacts in CT X-ray images are essentially caused by the above-discussed deviations of the radon data, which are detected for the reconstruction of voxel data, from the ideal mathematical model. Metal artifacts appear, for example, as dark or white lines, which radiate out from a metal part and in particular, extend between different metal parts.

In medical applications of computed tomography, metal artifacts are known as unwanted image distortions. For example, T. Koehler et al. in "A New Method for Metal Artifact Reduction in CT," published in "The International Conference in X-ray Computed Tomography," Salt Lake City, Utah, USA, 2011, proposes a method for removing metal artifacts from CT X-ray images.

It is known that the intensity and orientation of the metal artifacts that appear depend on the number of metal parts, the size of the metal parts, and the position of the metal parts to one another in the inspection object. The projection of an object with metal portions into a 3D CT X-ray image therefore requires the addition not only of metal artifacts, which would be caused by only the threat object, but also of the metal artifacts, which occur due to the interaction of the metal of the object and the metal that is already present in the luggage item. Likewise, metal artifacts should be visible in the threat object even if the threat object does not contain metal.

For the projection of an object into a CT X-ray image, N. Megherbi et al. have proposed a method that is supposed to achieve this. The known method is described in Najla Megherbi et al. "Fully automatic 3D Threat Image Projection: Application to Densely Cluttered 3D Computed Tomography Baggage Images," 2012, 3rd International Conference on Image Processing Theory, Tools and Applications (IPTA), pp. 153-159 and in N. Megherbi et al., "Radon Transform Based Metal Artefacts Generation in 3D Threat Image Projection," published in Proc. SPIE Optics and Photonics for Counterterrorism, Crime Fighting and Defence, volume 8901, pp. 1-7, SPIE, October 2013, DOI: 10.1117/12.2028506.

In the known methods, metal artifacts, which in a real luggage item would be caused in the CT X-ray image of the luggage item by metal of the object and possibly by its interaction with metal that is already present in the luggage item, are added essentially through a manipulation of the sinograms of the 3D CT X-ray image of the luggage item in the radon space and subsequent back-transformation into the image space; the radon transform of a plane (slice) of CT data from the image space is referred to here—using the English term—as a "sinogram." The object itself is inserted into the luggage item in the image space in that the voxels in the 3D CT X-ray image of the luggage item, which are associated with the object that is to be inserted, are attributed to the respective attenuation coefficient of the associated voxel of the object that is to be inserted.

FIG. 1 shows a schematic flowchart of the known image processing method proposed by Megherbi et al.

In a first step S1, for an inspection object such as a luggage item ("bag," B), first CT data B and associated second CT data BM ("bag metal," BM), which represent optional metal parts ("metal," M) already contained in the luggage item, are generated. In addition, third CT data TM ("threat metal," TM), which represent optional metal parts of a threat object ("threat," T) such as a weapon that is to be inserted into the first CT data B, are generated based on fourth CT data T of the threat object. The results of step S1 are the first CT data B, second CT data TM, third CT data BM, and fourth CT data T.

In a second step S2, the known radon transformation is used to transform planes (slices) from the first CT data B, the second CT data BM, and the third CT data TM from the image space BR into the radon space RR. The results of step S2 are first sinogram data SB of first sinograms for the first CT data B, second sinogram data SBM of second sinograms for the second CT data BM, and third sinogram data STM of third sinograms for the third CT data TM.

The intrinsically known "radon transformation" transforms images $f(x, y)$ in the image space BR $(x, y)$ into the radon space RR $(\alpha, s)$. In the latter, for each angle $\alpha$, the line integral of the function $f(x, y)$ along all lines s of the x-y plane is determined, where for each of these lines s, the radon transform Rf corresponds to a projection of the function $f(x, y)$ onto a perpendicular to the lines s. The superimposition of all of the projections (line integrals) yields the sinogram, a 2D data set. It follows from this that the radon space RR is therefore only two-dimensional at first. If this principle is applied to each plane of the 3D volume of a 3D CT X-ray image, then correspondingly numerous sinograms are obtained, namely one for each plane. The term "radon transformation" is understood here to always mean the "forward transformation" from the image space BR into the radon space RR. The reverse of the radon transformation is called the "radon back-transformation," "inverse radon transformation," or also "filtered back-projection" (since the implementation essentially consists of two steps, namely the filtration and transformation).

In a third step S3, the second sinogram data SBM are added to corresponding third sinogram data STM yielding respective fourth sinogram data SM. The results of step S3 are the fourth sinogram data SM for fourth sinograms, which represent all of the metal portions, namely the metal portions already contained in the luggage item and the fictitious metal portions of the threat object that is to be added.

In a fourth step S4, the fourth sinogram data SM are used to identify and—more or less in a reversal of a method known for medical CT systems for reducing metal artifacts—manipulate positions in the respectively associated first sinogram data SB, which positions are influenced by metal parts. In this case, the fourth sinogram data SM serve as a mask in order to determine whether or not metal is present on a particular sinogram beam in the inspection object with the fictitiously inserted threat object. In this connection, a sinogram beam is the line that the intensity data of a particular point in the associated (image) plane (slice) in the image space BR flow into. The first sinogram data SB are modified at the thus-identified positions a way that simulates the hardening due to metal. To that end, the respective values of the pixels in the first sinograms of the first sinogram data SB, which pixels have been identified as having been influenced by metal, are increased by being brought closer to a maximum value. These local modifications in the first sinogram data SB should cause the desired metal artifacts to appear in the back-transformation into the image space BR. In other words, at all positions in the first sinogram data SB, which are affected by metal in the inspection object (second sinogram data SBM) or metal in the threat object (third sinogram data STM), the first sinogram data SB of the inspection object are modified. The results of the fourth step S4 are modified first sinogram data SB*, which respectively contain the anomalies that are necessary for realistic and plausible metal artifacts, as would be contained in first sinogram data SB of real first CT data based on metal parts actually contained therein.

The inventors have realized that it is problematic that the first sinogram data SB of the original first CT data already include anomalies, which represent metal artifacts possibly already contained in the first CT data B. In the known method, these positions in the first sinogram data SB are likewise modified, as a result of which metal artifacts that are already present are unrealistically intensified.

In a fifth step S5, the modified fourth sinogram data SB* are transformed back into the image space BR by means of radon back-transformation. The results of step S5 are modified first CT data B* of the inspection object, which should include all of the necessary metal artifacts, namely artifacts for metal portions that are already contained in the inspection object, artefacts for metal of the threat object that is to be inserted, and the artifacts between all of these metal portions.

In a sixth step S6, the fourth CT data T are inserted into the modified first CT data B*, which do not yet contain the threat object itself. To that end, attenuation coefficients of the voxels of the modified first CT data B* are replaced with corresponding attenuation coefficients of associated voxels of the fourth CT data T of the threat object that is to be inserted. The results of step S6 are CT result image data FTI for the derivation of a fictitious threat image.

In the known method, the image quality of the result image is perceptibly altered. The X-ray image appears to be blurred and less richly detailed. Also in the known method, the metal artifacts that are already present in the original first CT data of the luggage item appear to be unnaturally intensified. These metal artifacts are conspicuous with even slight differences in the image quality in comparison to real X-ray images, even though the deviations are relatively minute so that in practice, the result images cannot be used for testing and training operators.

SUMMARY OF THE PRESENT DISCLOSURE

The present disclosure provides a production method and a corresponding production apparatus for inserting a fictitious target object into X-ray images that have been produced with a CT X-ray inspection unit, wherein the disadvantages discussed above in connection with the known method should be at least partially avoided or at least reduced.

The purpose of the production method and corresponding production apparatus is to produce test X ray images of inspection objects into which a fictitious target object has been inserted and is supposed to be found by an operator, for example for training and/or performance review purposes. The test X-ray images may be derived or produced based on CT data produced by means of CT in the form of 3D images or 2D images of an inspection object.

The test X-ray images produced may include both realistic and plausible metal artifacts, which are attributable to metal parts contained in the inspection object and metal portions of the fictitious target object that is to be inserted as well as the reciprocal influences thereof.

Metal artifacts already contained in an X-ray image may not be unrealistically intensified.

Furthermore, the influence on the image quality of the test X-ray images produced by the production method should be imperceptible as possible.

Features and details that are described in connection with the production method according to the present disclosure naturally also apply in connection with the production apparatus according to the present disclosure and vice versa. Thus in order to avoid repetition, reciprocal reference is hereby made with regard to the present disclosure of the individual aspects.

With regard to the known method described at the beginning in connection with FIG. 1 and its disadvantages, the present disclosure proposes an improved production method and a corresponding production apparatus for producing test X-ray images.

The new method avoids an unrealistic intensification of metal artifacts that are already present in the first CT data B and a reduction of the image sharpness of an X-ray obtained from the first CT data B. The term "image sharpness" is understood here to be a measure of the local contrast, i.e. how sharply the attenuation coefficients of adjacent voxels can differ in value. When CT data are transformed by means of radon transformation from the image space into a sinogram in the radon space and from there, are transformed back again, in an X-ray image that is derived from the CT data, this leads to a reduction in the local contrast (image sharpness). In other words, in the comparison to the original, a result image appears to be blurred and less richly detailed and thus less sharp. For example, this is caused by the fact that material property values, e.g. an attenuation coefficient and/or a material density value and/or an atomic number, of adjacent voxels have drawn closer in value through the double transformation. This reduces the local contrast. The reduction of the local contrast is noticeable as a perceptible reduction in the image sharpness; the image appears "washed out" or "blurred." In comparison to the known method—in which artifacts, which are to be added, are added into the first sinogram data SB of first sinograms of the inspection object—in the new method proposed here, only the actually missing artifact sinogram data, which represent the (metal) artifacts A that are to be added, are calculated in the radon space RR and, after back-transformation into the image space BR, are inserted into the original first CT data B.

In order to achieve this, the inventors have proposed producing new fourth sinogram data $SM^{}$ (corresponding to fourth sinograms), which essentially correspond to a logical subtraction of the third sinogram data STM (corresponding to third sinograms) minus the corresponding second sinogram data SBM (corresponding to second sinograms). As a result, the new fourth sinogram data $SM^{}$ contain only the points for which a corresponding point in an associated third sinogram is not equal to zero (STM< >0) and a corresponding point in the associated second sinogram is equal to zero (SBM==0). By means of the new fourth sinogram data $SM^{**}$, the points in the first sinogram data SB (corresponding to first sinograms) are identified in order to be able to alter/manipulate the intensity value of these points so that the influence of the metal that is to be fictitiously inserted into the inspection object is simulated in the first sinogram data SB. As a result, this avoids the situation of the artifact data, which are already contained in the first sinogram data SB and which represent the metal artifacts that are already present in the first X-ray image B, being unrealistically intensified as the method continues.

In the new method, it is not modified first sinogram data $SB^*$ that are produced, but only new artifact sinogram data SA, which represent only the metal artifacts that are actually to be added and that exist based on the metal of the target object and the interaction with metal that is possibly present. This is achieved in that the new fourth sinogram data $SM^{**}$ are used more or less as a mask to identify those pixels in the corresponding first sinogram data SB that belong to corresponding artifact sinogram data SA. All of the other pixels in the first sinogram data SB do not flow into the artifact sinogram data SA that are to be calculated. The intensity values that are present in the thus-identified pixels in the first sinogram data SB are manipulated in accordance with an empirically determined function so that an additional hardening by means of the fictitiously added metal of the target object is simulated for X rays passing through the inspection object.

The artifact sinogram data SA thus calculated in the radon space RR for metal artifacts that are to be added are transformed into the image space BR and can then be inserted into the original, i.e. unaltered, first CT data B. In other words, with the new method, not all of the first sinogram data $SB^*$, which have artifacts that have been added through manipulation in the radon space, are transformed back into the image space BR. The original first CT data are processed exclusively in the image space through the addition of the CT artifact data A and the fourth CT data T of the target object. As a result, the image sharpness of the 3D and/or 2D X-ray images that are derived from the modified first CT data B remains unchanged relative to an X-ray image that is derived from the original unaltered first CT data B.

A particular modification of the method relates to the insertion of the fourth CT data T, which represent the fictitious target object, and the CT artifact data A, which represent the metal artifacts that are to be added, into the first CT data B of the inspection object.

The fourth CT data T of a target object may be produced in advance. For this purpose, a target object can be held in position by means of a low-density support material such as polystyrene and its fourth CT data T are detected by means of a CT X-ray inspection unit. To this end, the support material can be positioned under the target object or can enclose it homogeneously and completely. The resulting fourth CT data T of the target objects can be kept in a database for subsequent use.

In the modification, the fourth CT data T of the target object that is to be inserted and/or the realistic and plausible CT artifact data A that are calculated for this purpose are used directly, without an labor-intensive freeing of the target object, and are inserted into the first CT data B of the inspection object. In this case, it is not just that material property values of a voxel in the first CT data B are replaced by corresponding material property values in the fourth CT data T of the target object or in the CT artifact data A that are to be added, but rather, a "blending" or "weighted combination" of the two material property values is carried out in a transition region as a function of the respective material property value of a voxel that is to be added. For example, the one value at 20% and the other value at 80% can flow into the new value; naturally, other weightings are also possible.

For example in one embodiment, by means of a suitable predetermined threshold in the fourth CT data T and/or in the CT artifact data A of the metal artifacts that are to be added, there is a differentiation between first voxels whose material property value lies below the predetermined threshold, second voxels whose material property value lies within a predetermined range above the predetermined threshold, and third voxels whose material property value lies above this predetermined range. The first voxels are interpreted as not belonging to the target object or as not being artifacts, for example are interpreted as being part of the background. In the fourth CT data T, for example, this is the support material. In other words, first voxels are ignored. Upon insertion into the first CT data B, second voxels with a material property value from within the predetermined range are respectively "blended" (weighted combination) with the material property value of the corresponding voxel therein. With third voxels, upon insertion into the CT data B of the inspection object, the material property value of the locally corresponding voxel is replaced by the material property value of the voxel belonging to the third voxel.

The above-described classification also enables a freeing of the metal parts in the inspection object or of the metal in a target object that is to be inserted, which is suitable for the above-explained method for producing the artifacts. In other words, by means of predetermined thresholds, the new method can automatically detect metal portions of the target object and metal portions of the inspection object or artifacts that are to be added and can differentiate them from non-metallic components.

A first aspect of the present disclosure relates to a production method for test X-ray images. In principle, the method includes:
preparation of first computed tomography (CT) data B that represent an inspection object, second CT data BM that represent metal portions contained in the inspection object, and third CT data TM that represent metal portions of a target object, which is to be inserted into the first CT data B;
transformation of the first, second, and third CT data B, BM, TM from the image space into corresponding first sinogram data SB, second sinogram data SBM, and third sinogram data TM in the radon space;
calculation of the artifact sinogram data SA in the radon space, which represent metal artifacts that are to be added to the first CT data B based on the target object that is to be inserted;
back-transformation of the artifact sinogram data SA from the radon space into the image space in CT artifact data A, which represent the artifacts that are to be inserted; and
insertion of the CT artifact data A into the first CT data B.

The inspection objects and target objects may be scanned with a CT X-ray inspection unit.

The production method may also include: insertion of fourth CT data T, which represent the target object, into the first CT data B in order to obtain CT test image data FTI.

The production method may also include: derivation of CT X-ray images and/or 2D X-ray images of the inspection object from the CT test image data FTI. The 3D CT X-ray images and/or 2D X-ray images of the inspection object can be used as test X-ray images, for example for training and/or testing operators of an X-ray inspection unit.

It should be noted that the production method can basically be embodied to produce a particular 2D X-ray image with an inserted fictitious target object. To this end, it is in principle enough to carry out the method only for the affected image plane, i.e. a particular slice in the first CT data B and correspondingly in the second, third, and fourth CT data BM, TM, and T.

One possible representation of the associated CT data is a three-dimensional (3D) computed tomography (CT) X-ray image or a two-dimensional (2D) X ray image.

CT data can be obtained by means of CT for a scanned object, e.g. the inspection object and the target object that is to be inserted. In the CT scanning process, first radon data of the object are detected. The radon data (or sinogram data) can be transformed by means of filtered back-projection into CT data of the object. In other words, CT data are essentially a 3D data set, in which individual volume elements (voxels) of the object are each associated with a material property of the material at the position of the voxel.

Sinograms in the radon space are essentially one possible representation of the radon data, which include the intensity data that are detected during the scanning of an object by means of CT. In principle, in the CT, an object is penetrated in a plane (slice) by X-rays produced by a point source of X rays, from a plurality of projection directions. In this connection, for each projection direction in this plane, on an opposing detector behind the object, an associated intensity profile is obtained, which corresponds to a perspective projection of the object. If the X-ray source and the detector are rotated around the object, this correspondingly yields the respective associated intensity profile for the plurality of projection directions. If the intensity data that are detected in this way are plotted over the projection direction and the detector width in the form of a Cartesian coordinate system, this yields a sinogram as one possible graphic representation of the detected radon data (sinogram data).

For each pixel (p) of an associated SA, a modified intensity value is calculated in accordance with the following rules:
(i) $SA(p)=(q\ \mu-q\ SB(p))$ if $STM(p)\neq 0$ and $SBM(p)=0$ and
(ii) $SA(p)=0$ otherwise,
where q is a predetermined value between 0 and 1 and where $\mu$ is the maximum in the associated second sinogram data.

The factor q can be a value between 0.02 and 0.06. The factor q may be a value between 0.03 and 0.04. Particularly, the factor q may be equal to 0.04.

The insertion of CT artifact data A and/or fourth CT data T into the first CT data B can include: blending or weighted combination of a material property value, which is associated with a particular voxel in the first CT data B, as a function of a respective material property value, which is associated with a corresponding voxel of the CT data A, T that are to be added, wherein corresponding spatial coordinates are associated with the corresponding voxel and the particular voxel.

The insertion of CT data A, T into the first CT data B may include:
- classification, by means of a predetermined threshold in the CT data (T, A) to be added, of first voxels whose material property values lie below the predetermined threshold, second voxels whose material property values lie in a predetermined range above the predetermined threshold, and third voxels, whose material property values lie above this predetermined range;
- ignoring of the CT data of the first voxels;
- blending of the material property value, which is associated with a particular voxel of the first CT data, with the material property value of a corresponding second voxel of the CT data that are to be inserted; and
- replacement of the material property value, which is associated with a particular voxel of the first CT data, with a material property value, which is associated with a corresponding voxel of the CT data that are to be added,
- wherein in the step of the blending and in the step of the replacement, corresponding spatial coordinates are associated with the corresponding voxel and the particular voxel.

The CT data B may include one value for a material property; and coordinates for determining (the position) of a volume element (voxel), which is associated with at least one value for a material property. The material property associated with the respective voxel may be at least one of: an absorption coefficient, a material density value, and an atomic number. The coordinates for identifying a voxel may be three-dimensional (3D) coordinates, which identify the position of the voxel in space.

A second aspect of the present disclosure relates to a computer program product having a computer program, which has software means for carrying out a method according to the first aspect of the present disclosure when the computer program is run in an automation system such as a computer system.

A third aspect of the present disclosure relates to a production apparatus for producing test X-ray images, the production apparatus including: an inspection object database for storing produced first CT data B of inspection objects; a target object database with fourth CT data T and possibly third CT data TM of target objects; and an image projection unit for projecting a target object from the target object database into an X-ray image from the inspection object database in order to produce a test X-ray image, wherein the image projection unit is set up to carry out a method according to the first aspect of the present disclosure. The production apparatus may have an automation system, for example a computer system, for carrying out the method according to the first aspect.

The production apparatus can also include an updating unit for the inspection object database. The updating unit can be set up to update the inspection object database in that first CT data B, which are older than a predetermined time span and/or have been used for a certain number of times, e.g. once, to produce CT test image data FTI, are deleted from the inspection object database or are disabled for further use. The image projection unit can also be set up to store test X-ray images in a test X-ray image database. The updating unit and/or the image projection unit can be setup to update CT test image data FTI in the database in that CT test image data FTI, which are older than a second time span and/or have been used for a certain number of times, e.g. once, for training or testing an operator, are deleted or are disabled for further use.

The production apparatus can be part of an X-ray inspection unit or can be communicatively and/or operatively connected to it in order to enable "live" training and/or testing of operators. The CT test image data of inspection objects may be produced with an X-ray inspection unit at the respective screening point.

A fourth aspect of the present disclosure relates to a central control unit for at least one X-ray inspection unit for nondestructive inspection of an inspection object, particularly of a luggage item or other package, having a production apparatus according to the third aspect, wherein the control unit may be connected to the at least one X-ray inspection unit via a communication network.

The central control unit may have at least one display unit for displaying X-ray images of a current inspection object for visual inspection by an operator or for displaying a test X-ray image. The central control unit may be positioned relative to the at least one X-ray inspection unit in such a way that an inspection object, which is currently to be screened with the at least one X-ray inspection unit, is not visible to an operator.

A fifth aspect of the present disclosure relates to an X-ray inspection unit for nondestructive inspection of an inspection object, particularly of a luggage item or other package, which has a central control unit according to the fourth aspect or is operatively and communicatively connected thereto.

Based on X-ray images, which have been produced by an X-ray inspection unit, an operator can find target objects in an inspection object. The X-ray inspection unit can, for example, be a CT X-ray inspection unit of the kind that are used, for example, at security checkpoints, e.g. at entrances to security zones or in a luggage handling system, for example at airports, to manually or automatically conduct nondestructive inspection of luggage items and/or freight goods, which are to be loaded on board an aircraft. X-ray inspection units can also be used at other checkpoints, e.g. at entrances to security-relevant areas or buildings, at border inspection posts, etc. for inspecting objects such as hand luggage that people are bringing along with them or postal packages such as letters, packages, and parcels.

The goal of the inspections is to discover certain target objects. Target objects can be objects or sub-stances with hazard potential, such as weapons, explosives, chemicals etc., i.e. dangerous objects. Target objects can also be objects or substances that do not initially pose an immediate threat. Target objects can, for example, be data carriers such as DVDs or CD-ROMs, smuggled goods, money, drugs, etc. Target objects can also basically be objects that are not hazardous, but are classified as dangerous objects for certain reasons, e.g. Li-ion batteries. Target objects can be foods subject to an import prohibition. Basically, any objects can be defined as target objects, e.g. for training operators. A target object is thus basically understood as an object or substance, which an operator is supposed to detect in X-ray images of an inspection object. For these purposes, corresponding CT image data of target objects can be produced and kept in a target object database.

With the method proposed here, realistic CT test image data FTI can be produced and in the course of operation, can be used for testing operators of X-ray inspection units or used for training them. Because of the above-described novel production of the CT test image data FTI, these data contain both realistic and plausible metal artifacts like they would exhibit in real CT X-ray images of an inspection object that actually contains the target object. In addition, the CT FTIs produced with the proposed method do not contain any alterations in the image sharpness and for this reason, are not identifiable as FTIs.

A sixth aspect of the present disclosure relates to a luggage or package screening system having at least one X-ray inspection unit and a central control unit according to the fourth aspect.

BRIEF DESCRIPTION OF THE FIGURES

Other advantages, features, and details of the present disclosure ensue from the following description in which exemplary embodiments are described in detail with reference to the drawings. The features mentioned in the claims and/or in the description can, each by themselves or in any combination, be essential. Likewise, the features mentioned above and the features explained in greater detail below can be used each by themselves or in any of a plurality of combinations. Some parts or components with similar or identical functions have been provided with the same reference numerals. The terms "left," "right," "above," "below" used in the description of the exemplary embodiments relate to the drawings in an orientation with a normally legible figure description and normally legible reference numerals. The exemplary embodiment that are shown and described are not to be understood as exclusive and are instead exemplary in nature for explanatory purposes. The detailed description serves to provide information to the person skilled in the art; for this reason, known circuits, structures, and methods are not portrayed or explained in detail in the description.

EXEMPLARY EMBODIMENTS

Figure 1:
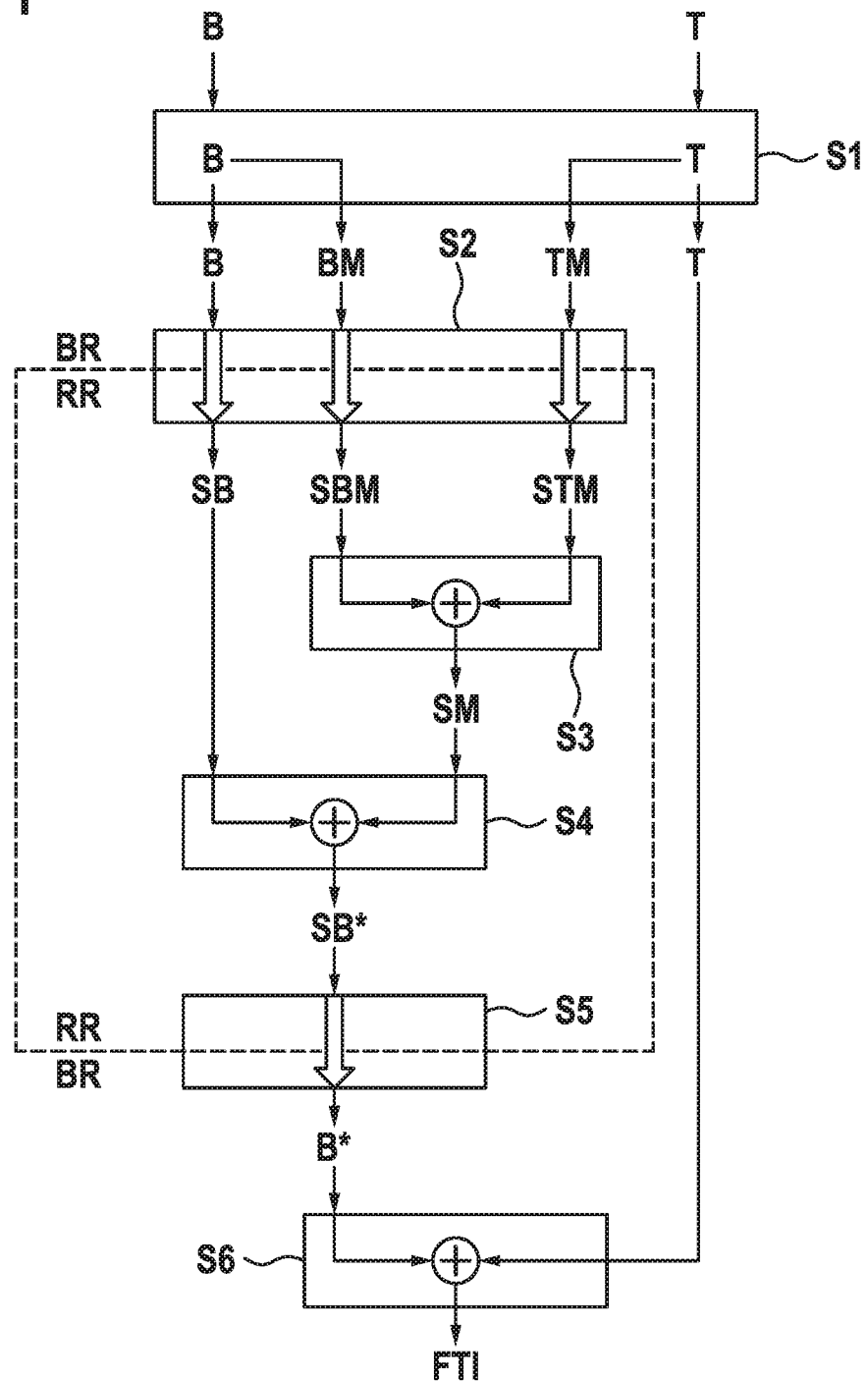
FIG. 1 shows a schematic flowchart of a known method for inserting fictitious threat objects into CT X-ray images.
Figure 2:
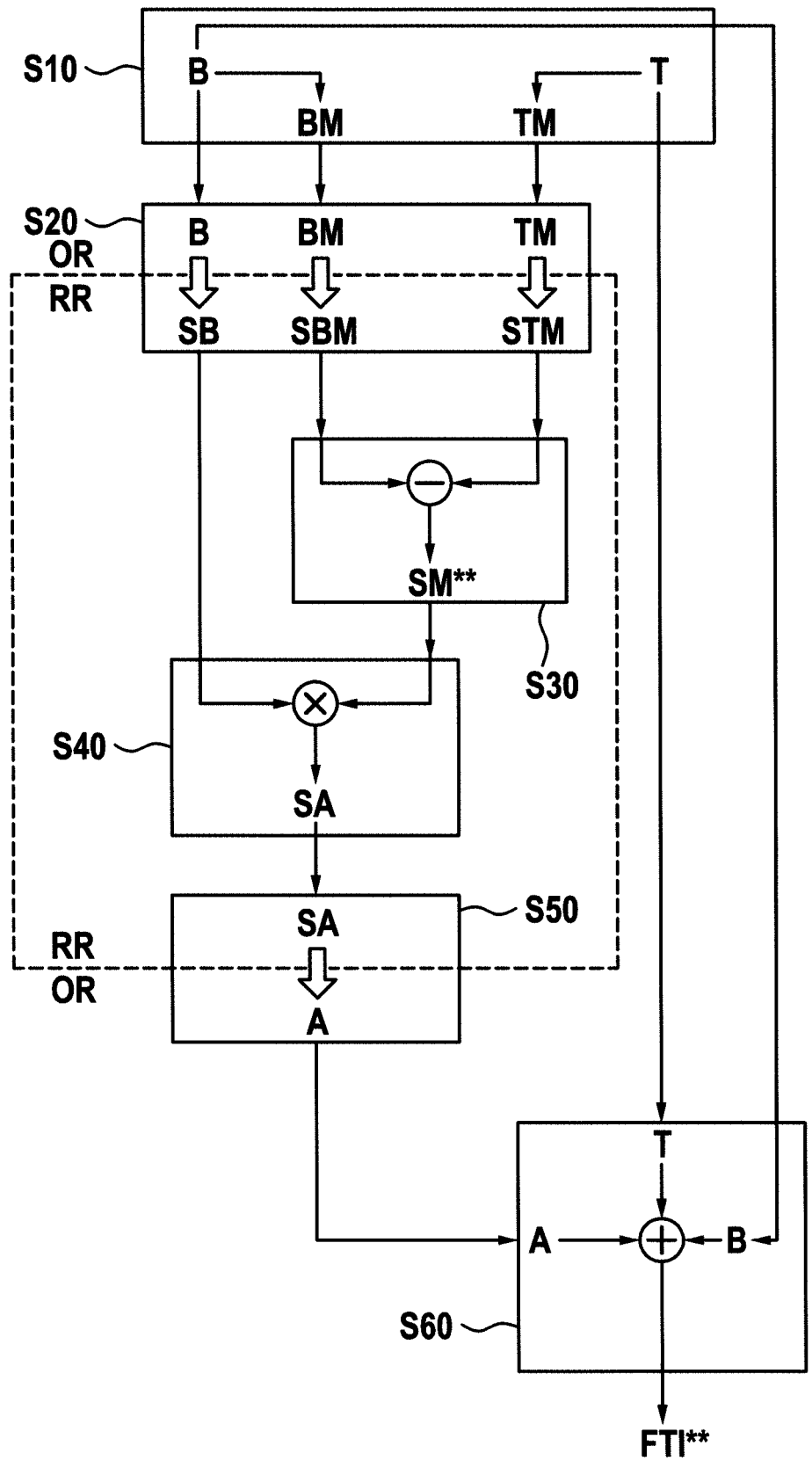
FIG. 2 shows a schematic flowchart of an exemplary embodiment for a method according to the present disclosure for inserting fictitious target objects into CT X-ray images.

FIG. 2 shows a schematic flowchart of an exemplary embodiment for the new method proposed here for inserting fictitious target objects into CT X-ray images.

In a first step S10, a first CT-X-ray image of an inspection object is produced, i.e. first CT data B of the inspection object, for example a luggage item. Based on the CT data B of the inspection object, an associated second CT-X-ray image is produced, i.e. second CT data BM, with optional metal portions, which are possibly already contained in the luggage item. In addition, a third CT-X-ray image is produced, i.e. third CT data TM, with optional metal portions of a target object, which is to be inserted into the first CT-X-ray image. The third CT X-ray image, i.e. the third CT data TM, is produced based on a fourth CT X-ray image, i.e. fourth CT data T, of this target object.

The results of the first step S10 are thus the first CT data B, the second CT data BM, the third CT data TM, and the fourth CT data T.

Figure 4:
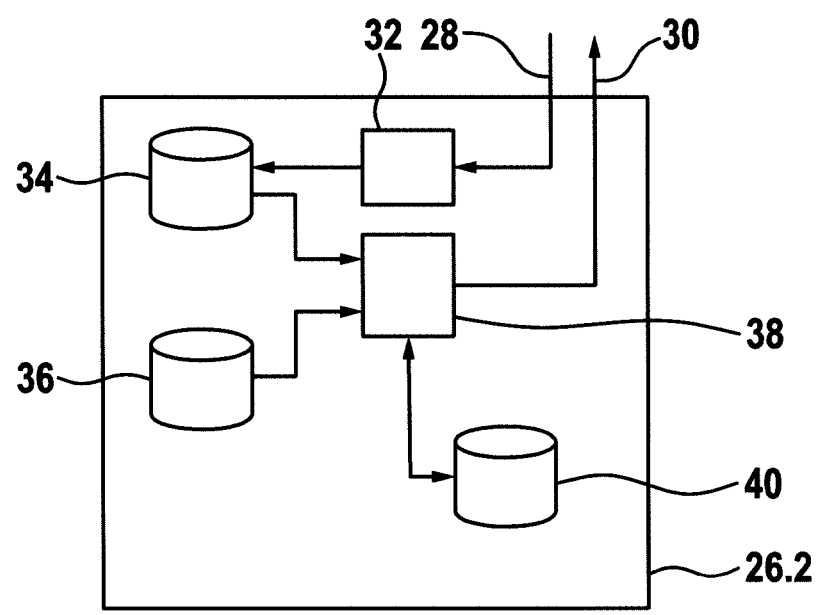
FIG. 4 shows an exemplary embodiment of a production apparatus for 3D CT test X-ray images.

The fourth and/or third CT data TM, T of target objects can already be produced in advance and kept in a target object database for further use (for example cf. reference numeral 34 in FIG. 4).

In a second step S20, through the use of the known radon transformation, the first CT data B, the second CT data BM, and the third CT data TM are transformed from the image space BR into the radon space RR. As a result, corresponding first sinogram data SB for the first CT data B, second sinogram data SBM for the second CT data BM, and third sinogram data STM for the third CT data TM are obtained.

In a third step S30, based on second sinogram data SBM and respectively corresponding third sinogram data STM, respective new fourth sinogram data SM are produced. The new fourth sinograms essentially correspond to a combination in the sense of a logical difference in order to determine exclusive points of the third sinogram data STM. The new fourth sinograms contain only the pixels for which (exclusively) the corresponding pixel in the associated third sinogram is not equal to zero, i.e. STM< >0 and at the same time, the corresponding pixel in the associated second sinogram is equal to zero, i.e. SBM=0. This avoids the situation of artifact data (=SBM), which represent the metal artifacts that are already present in the first 3D CT-X-ray image, being unrealistically intensified as the method continues. The results of the third step S30 of the new method are new fourth sinogram data SM, which exclusively represent metal parts of the threat object that is to be added.

In a fourth step S40, the new fourth sinogram data SM are used to identify the corresponding pixels of a respective first sinogram SB as the positions that are influenced by the metal parts that are to be added. At these identified positions, the respective intensity data that are present there are manipulated in order to produce the new artifact sinograms. So that the new method does not produce modified first sinograms, but instead only the new artifact sinogram data SA, which represent only the metal artifacts A that are actually to be added due to metals of the target object and due to the interaction with possibly present metal, other intensity data of the respective first sinogram data SB do not flow into the associated new artifact sinogram. This is achieved in that with the new fourth sinogram data SM functioning as a mask, those points in the first sinograms are identified, which flow into the new artifact sinogram, while all other positions of the first sinogram do not flow into the artifact sinogram. For all of the identified positions in the first sinogram data SB, a hardening by means of metal of the intensities that are present at these positions in the first sinograms is calculated for the X-rays passing through the inspection object.

The steps S30 and S40 may be performed together. For example, to produce an artifact sinogram SA for each pixel p, an intensity value SA(p) can be calculated in accordance with the following rules according to the present disclosure:
(i) $SA(p)=(q \mu -q\, SB(p))$ if $STM(p)\neq 0$ and $SBM(p)=0$ and
(ii) $SA(p)=0$ otherwise,
where q is a predetermined value between 0 and 1 and $\mu=\max(SBM)$. Rule (i) identifies and modifies those pixels of the respective first sinogram that can be associated with metal parts. Rule (ii) ensures that no pixels from the first sinograms, which cannot be associated with the metal that is to be fictitiously added, flow into the new artifact sinogram. The value q can be a value greater than or equal to 0.02 and less than or equal to 0.06. The value q may be a value greater than or equal to 0.02 and less than or equal to 0.06. In one embodiment, the value q is equal to 0.04.

In a particular way, the method according to the present disclosure avoids an influence on the metal artifacts, which are already contained in the first 3D CT-X-ray image B and which are caused by the metal parts that are already contained therein. For this purpose, in a second modification step, only the metal artifacts, which are additionally attributable to the metal in the target object and to the interactions of this metal with the metal parts that are already present, are produced by the method according to the present disclosure.

The results of the fourth step S40 are thus novel artifact sinogram data SA, which respectively contain the necessary anomalies for the metal artifacts that are to be added and which are also contained in first sinogram data SB of real CT data based on metal parts that are actually contained.

In a fifth step S50, the artifact sinogram data SA, which are calculated in the radon space RR, for artifacts that are to be added are back-transformed into the image space BR so that CT data A for the artifacts that are to be added are contained in the image space BR.

In a sixth step S60, the CT data A with the artifacts, which are to be added, and the fourth CT data T for the target object, which is to be added, are inserted into the original first CT data B. The results of the sixth step S60 are CT test image data FTI for the inspection object with an inserted fictitious target object. Based on the CT test image data FTI, corresponding 3D CT X-ray images or corresponding 2D X-ray images of the inspection object can be derived for further use. The resulting 3D CT X-ray images or 2D X-ray images are improved significantly with regard to the plausibility and realistic appearance of the metal artifacts and with regard to the image sharpness as compared to those that were obtained with the known method.

Figure 3:
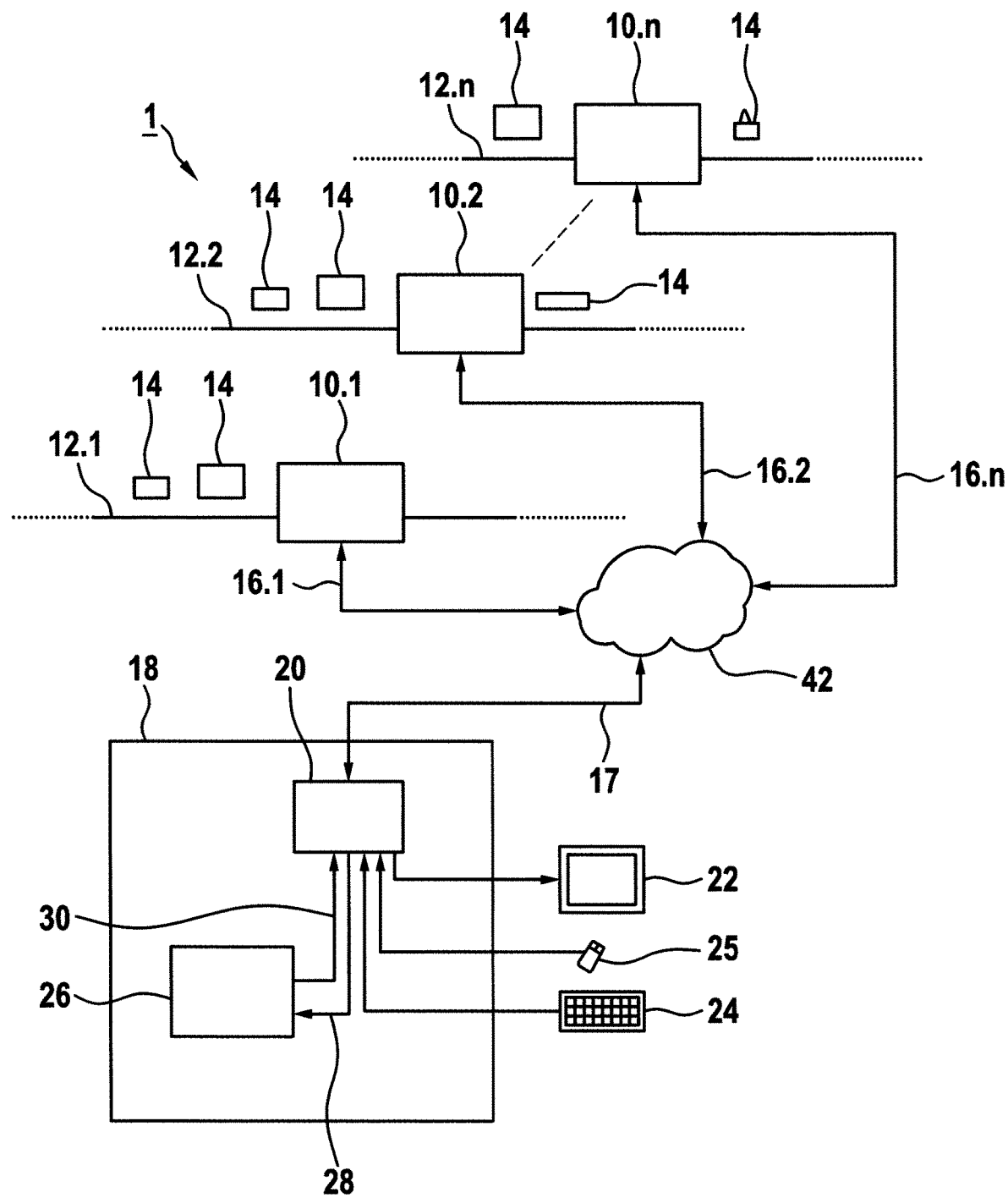
FIG. 3 shows an automatic luggage or package screening system in a schematic depiction in the form of a block diagram.

FIG. 3 shows an automatic luggage or package screening system 1 (for short: screening system 1) of the kind that is used, for example, at airports for level-2 luggage items or packages. In that context, luggage items or packages, for example, which are brought by third parties or passengers for loading into the hold of an aircraft, are inspected as inspection objects. It should be noted that the threat objects (TIP) that are discussed here in connection with the image projection can basically be used in connection with all embodiments of X-ray inspection units.

The screening system 1 includes a number n of intrinsically known CT X-ray inspection units 10.1, 10.2, and 10.n, which are each schematically indicated by a rectangle. On conveyor belts 12.1, 12.2, and 12.n, which are associated with the respective CT X-ray inspection unit 10.1, 10.2, and 10.n, luggage items or packages are each transported as inspection objects 14 through one of the CT X-ray inspection units for automatic inspection. The CT X-ray inspection units 10.1, 10.2, 10.n function according to the known CT principles and need not be explained in greater detail here.

All of the CT X-ray inspection units 10.1, 10.2, 10.n of the screening system 1 are networked via respective data connections 16.1, 16.2, and 16.n by means of a data network 42 with at least one central control unit 18 that is spatially remote from the individual X-ray inspection units 10.1, 10.2, and 10.n. The central control unit 18 itself is connected to the data network 42 via a corresponding data connection 17.

The central control unit 18 is the workstation of an operator. A display unit 22 is provided for visual inspection of X-ray images of an inspection object. For example, if one of the X-ray inspection units 10.1, 10.2, 10.n cannot automatically decide about the harmlessness of an inspection object 14, then the operator is shown the X-ray image or X-ray images of the inspection object in question on the display unit 22. In other words, if the inspection routines implemented in the X-ray inspection units 10.1, 10.2, 10.n, based on one or more X-ray images of a current inspection object 14, cannot establish with the required degree of certainty that no target object, e.g. a hazardous substance, is contained in the inspection object 14, then the responsible operator must conduct a visual inspection by means of the display unit 22. The operator then decides, for example, whether the involved inspection object must be opened and undergo a manual inspection.

The control unit 18 has input means 24 such as a keyboard and/or individual input keys, control elements such as a joystick, a mouse, a trackball, or the like. It is therefore possible for the operator to perform control interventions, etc. in the usual and customary fashion. The central control unit 18 also accommodates the hardware and software, which are required for the functions described here, of a conventional and thus known data processing system 20 (computer system). In other words, all of the functions described below can essentially be implemented by means of an intrinsically known data processing system 20, in one computing unit or distributed over several of them. The data processing system 20 is then essentially configured, i.e. programmed in the usual way, to perform the described functions and method or parts thereof.

The data processing system 20 usually includes (not shown): one or more processors serving as a central computing unit as well as internal memory and/or external memory, which is nonvolatile for the software and is set up in the form of a RAM (random-access memory) for working data. For interaction with functional components of the device, the data processing system 20 is connected via communication interfaces, for example to the data network 42 that includes the individual CT X-ray inspection units 10.1, 10.2, 10.n. As an input/output interface for interaction with the operator, the one screen 22 or more screens serve(s) as (a) display unit(s) and the keyboard 24 and/or mouse 25 serve(s) as (an) input unit(s).

It should also be noted that the above-described functions and method can be implemented for execution entirely by means of a computer program or entirely on the hardware level as well as in any mixed form between hardware and software. For image processing sequences, for example when projecting an image of a threat object (TIP) into an X-ray image of an inspection object, all or some of the method steps can also be implemented by specialized image-processing hardware such as graphics processing units (GPUs) in corresponding programming commands.

In order to produce test X-ray images for training or testing an operator, a production apparatus 26 for CT test X-ray images is provided, which is set up to produce CT test X-ray images in the form of an FTI, which may be based on inspection objects that have been recently inspected on site and to display them for the training and/or testing of an operator. The CT test X-ray images produced with the TIP method explained here in connection with FIG. 2 can be referred to as pseudo FTIs.

FIG. 4 shows an exemplary embodiment of the production unit 26 with an updating unit 32, which is connected to the data processing system 20 of the control unit 18 via a data line 28. Via the data line 28, the updating unit 32 is sent updated [sic] in the course of operation of the CT X-ray inspection units 10.1, 10.2, 10.n of the screening system 1.

The updating unit 32 can be set up to store CT X-ray images of inspection objects, which have been inspected on site in the screening system 1, in an inspection object database 34. The updating unit 32 can also be set up to update the inspection object database 34 so that an X-ray image stored therein is no older than a predetermined second time span and/or an X-ray image stored therein is deleted or disabled for further use once it has been used a predetermined number of times, for example once, for producing a CT test X-ray image. This achieves that only contents that are plausible for the respective time period are contained in the inspection objects, which serve as a basis for an FTI; for example, a suitcase in the middle of summer that contains objects that are typical for winter would be conspicuous for this reason alone.

The production unit 26 is also provided with a target object database 36 in which is stored a library of fourth CT data T (and possibly third CT data TM) of target objects. The target object database 36 stores image data of those target objects, which should be found by the screening system 1, but especially by an operator, inside the inspection objects. The target objects can be the objects that have already been explained above.

An image projection unit 38 is set up to project a virtual target object from the target object database 36 into first CT data B of the inspection object database 34 in order to produce CT test image data FTI. A test X-ray image produced in this way can be provided by the test X-ray image production unit 26 via a data line 30 to the data processing system 20 of the control unit 18.

The data processing system 20 is set up to randomly display a 3D test-X-ray image or 2D test X-ray images to an operator in the course of operation, in accordance with the applicable legal provisions, for example without notice or warning, in order to test the training level, detection capabilities, and possibly attentiveness of an operator.

With regard to the capabilities of the system in connection with the image projection of threat objects and/or prohibited substances, in order to avoid repetition, reference is made to (EU) Regulation no. 185/2010 of 4 Mar. 2010 for establishing detailed measures for the implementation of the common basic standards on aviation security, in particular items 11.4 and 12.5 thereof. For the sake of completeness, it should be noted that TIP is also a requirement in corresponding regulations outside of the European Community.

The production unit 26 can also be provided with a test X-ray database 40 in which test X-ray images produced by the image projection unit 38 can be stored. The image projection unit 38 can then be additionally set up to manage test X-ray images FTI in in the test X-ray image database 40 so that test X-ray images, which are older than a predetermined time span and/or that have been used for a certain number of times, for example once, are deleted or disabled for further use. Consequently, a large number of test X-ray images in the test X-ray image database 40 can be produced ahead of time in the course of operation. The test X-ray image database 40 can be updated in a way that is similar to the one described in connection with the inspection object database 34. As a result, the management measures can achieve the fact that when testing operators, test X-ray images, which may already be known to the operators, are not used.

The above-described system can produce test X-ray images in the form of fictitious threat images (FTI) by using actual CT data of real inspection objects that have been inspected on site. The test X ray images essentially correspond to X-ray images of real luggage items into which a real threat object has been inserted ahead of time; such test images are referred to as so-called combined threat images (CTI). In this way, it is possible to avoid disadvantages of the FTI and CTI concepts; in particular, the ongoing operation of the screening system 1 is not negatively affected. As a result, operators do not become accustomed to a particular selection of test X-ray images. Because of the continuous updating of the test X-ray image database 40, it is unlikely that an operator will be confronted with a test-X-ray image several times. If the production of test X-ray images uses only X ray images that originate from inspection objects that have been inspected on site, this assures that luggage items or packages are used, which are typical for the screening point and for the conditions currently prevailing at the screening point, for example the time of year. Essentially, it is ensured that every possible distinctive feature of inspection objects, which are typical for the screening point, also appear in the test X-ray images. As a result, the test X-ray images cannot appear "suspicious" to an operator due to consciously or unconsciously perceptible deviations from site-specific X-ray images.

Since the new production method for the test X-ray images in the radon space RR exclusively produces artifact sinogram data SA, which represent only metal artifacts A that have yet to be added to the first CT data B, distinctive features of the test X-ray images produced with it, which are discussed above in connection with the known method, are avoided. With the new method, in the radon space, only sinogram beams, which represent metal artifacts that are not yet contained in the first CT data B, are modified, i.e. those metal artifacts, which are attributable to the metal of the target object and the interaction of the metal of the target object with metal parts that re already contained in the inspection object. This avoids the situation of the metal artifacts, which are possibly already present in the first CT data B, being additionally intensified. In addition, only the new artifact sinogram data SA are transformed back into the image space by means of radon back-transformation. The CT artifact data A that are thus present in the image space are inserted into the first CT data B of the inspection object in the image space. In other words, with the new method, only new artifacts A are calculated and added to the image space, while in the known method, artifacts in the radon space are added to the first sinogram data SB and the entire modified first X-ray image must be calculated due to back-transformation into the image region. In other words, in the new method, it is not necessary to transform any modified first sinogram data SB* from the radon space back into the image space.

With the new method, fourth CT data of the target object and the calculated CT artifact data A are finally inserted into the original first CT data B in the image space and the new fictitious CT test image data FTI** are obtained, from which 3D and/or 2D X-ray images of the inspection object can be derived as needed.

The new method achieves the fact that new fictitious test X-ray images—with undistorted, already present metal artifacts as well as the metal artifacts that are to be added and the inserted target object—have the same image sharpness as an original X-ray image based on the original first CT data B.

Figure 5A:
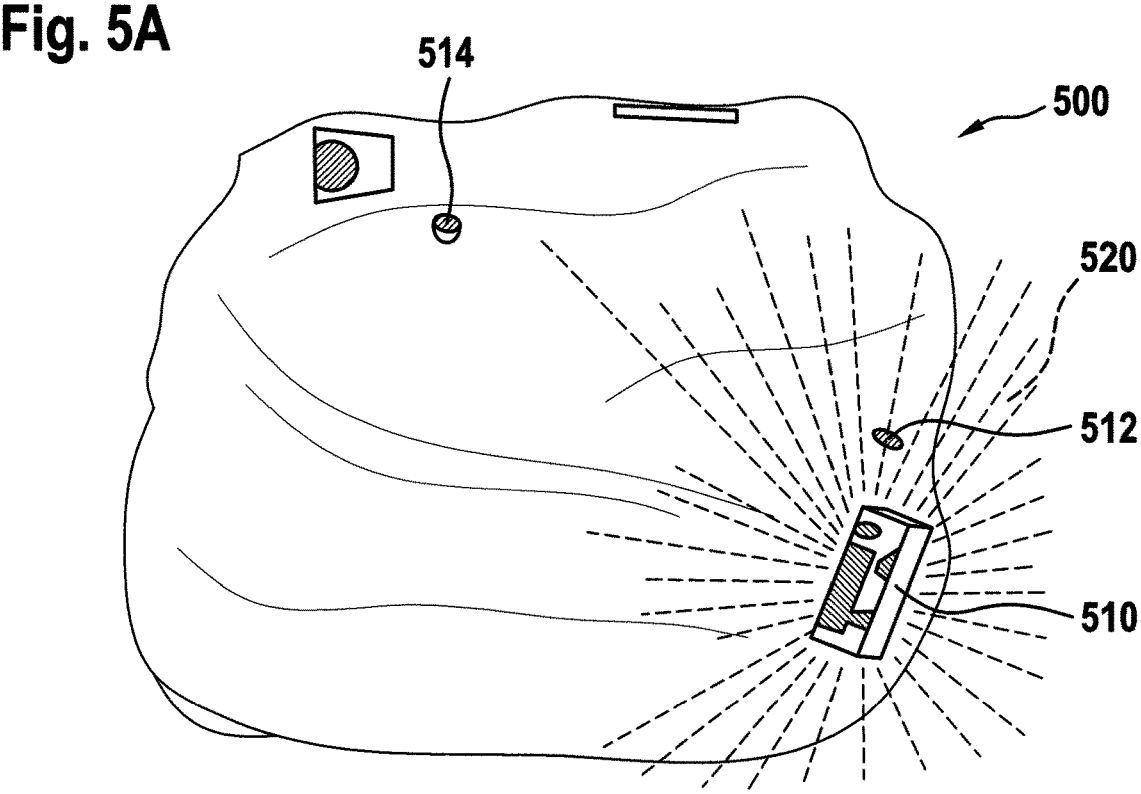
FIG. 5A shows an original 3D CT-X-ray image of a luggage item as an example for an inspection object with several metal artifacts, which are caused by metal parts in the luggage item.

FIG. 5A shows an original 2D X-ray image 500 of a luggage item as an example for an inspection object with metal artifacts 520, which are caused by metal parts 510, 512, 514 contained in the luggage item. The metal artifacts 520 are essentially caused by the metal part 510 and appear in the form of rays extending out from the metal part 510.

Figure 5B:
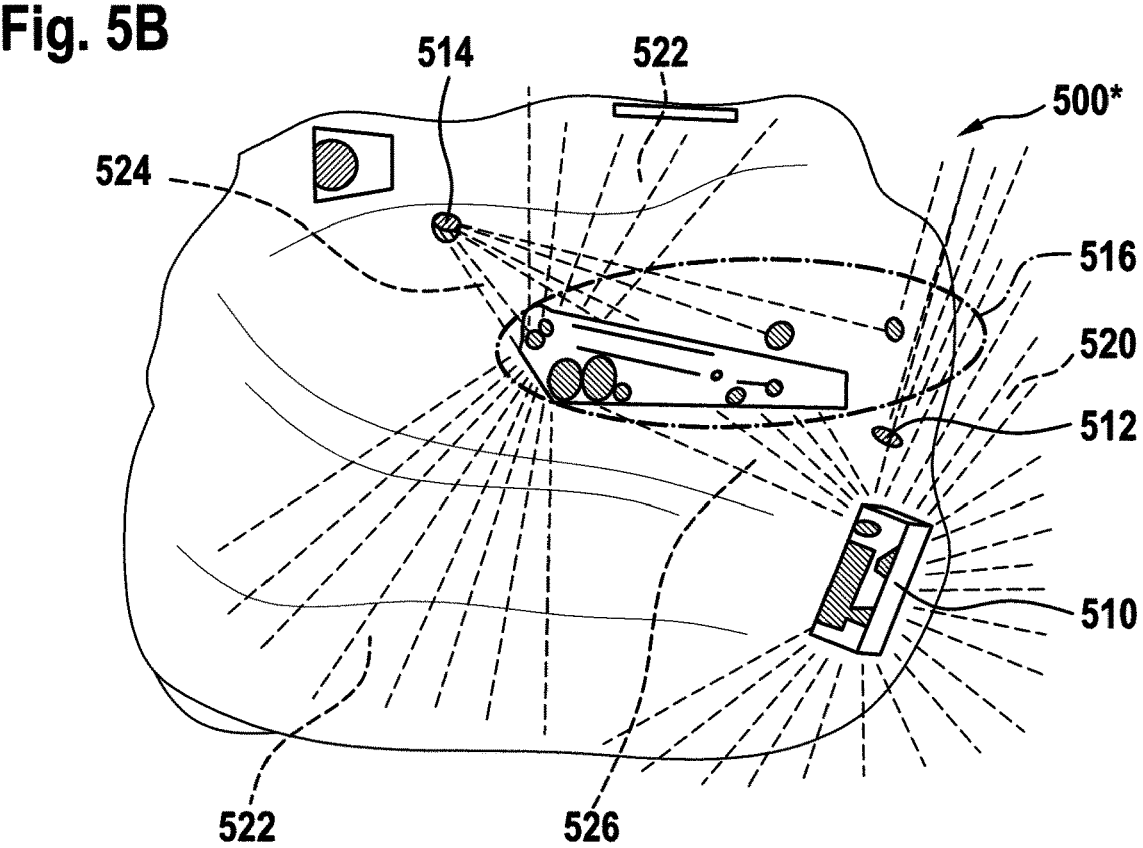
FIG. 5B shows the 3D CT-X-ray image of FIG. 5a into which a threat object functioning as a target object and the metal artifacts, which have been produced according to the present disclosure, are inserted.

FIG. 5B shows the X-ray image from FIG. 5A, into which a threat object with metal portions/parts 516 has been inserted as a target object along with the metal artifacts 522, 524, 526 thereof, which have been produced according to the present disclosure. Because of the fictitiously inserted metal parts 516, metal artifacts 522, which are caused solely by the metal part 516, and metal artifacts 524 and 526, which are attributable to the interaction of the already present metal parts 510, 512, 514 with the fictitiously inserted metal parts 516, must likewise be inserted into the X-ray image so that it is realistic and plausible. The present disclosure achieves all of the above.

The invention claimed is:

1. A production method for test X-ray images, the method comprising:
   preparation of first computed tomography (CT) data (B) that represent an inspection object, second CT data (BM) that represent metal portions contained in the inspection object, and third CT data (TM) that represent metal portions of a target object, which is to be fictitiously inserted into the first CT data (B);
   transformation of the first, second, and third CT data (B, BM, TM) from the image space (BR) into corresponding first sinogram data (SB), second sinogram data (SBM), and third sinogram data (STM) in the radon space (RR);
   calculation of fourth sinogram data (SM) in the radon space (RR) based on the second sinogram data (SBM) and the third sinogram data (STM), the fourth sinogram data (SM) corresponding to a logical subtraction of the third sinogram data (STM) minus the corresponding second sinogram data (SBM);
   calculation of the artifact sinogram data (SA) in the radon space (RR), which represent metal artifacts that are to be added to the first CT data (B) based on the target object that is to be inserted and further based on the fourth sinogram data (SM**);
   back-transformation of the artifact sinogram data (SA) from the radon space (RR) into the image space (BR) in CT artifact data (A), which represent the artifacts that are to be inserted; and
   insertion of the CT artifact data (A) into the first CT data (B).

2. The production method according to claim 1, further comprising insertion of fourth CT data (T), which represent the target object, into the first CT data (B) in order to obtain CT test image data (FTI).

3. The production method according to claim 2, further comprising derivation of at least one of 3D X-ray images and 2D X-ray images of the inspection object from the CT test image data (FTI).

4. The production method according to one of claim 1, wherein for each pixel (p) in an associated artifact sinogram, an intensity value (SA(p)) is calculated in accordance with the following rules:
   (i) SA(p)=(q μ–q SB(p)) if STM(p)..0 and SBM(p)=0 and
   (ii) SA(p)=0 otherwise, where q is a predetermined value between 0 and 1 and μ is the maximum in the associated second sinogram data.

5. The production method according to claim 4, where q is a value between 0.02 and 0.06.

6. The production method according to claim 1, wherein the insertion of CT data (A, T) into the first CT data (B) comprises:
   weighted combination of a material property value, which is associated with a particular voxel in the first CT data (B), as a function of a respective material property value, which is associated with a corresponding voxel of the CT data that are to be added, wherein corresponding spatial coordinates are associated with the corresponding voxel and the particular voxel.

7. The production method according to claim 6, wherein the insertion of CT data (A, T) into the first CT data (B) also comprises:
   classification, by means of a predetermined threshold in the CT data (T, A) to be added, of first voxels whose material property values lie below the predetermined threshold, second voxels whose material property values lie in a predetermined range above the predetermined threshold, and third voxels, whose material property values lie above this predetermined range;
   ignoring of the CT data of the first voxels;
   weighted combination of the material property value, which is associated with a particular voxel of the first CT data (B), with the material property value of a corresponding second voxel of the CT data that are to be inserted; and
   replacement of the material property value, which is associated with a particular voxel of the first CT data (B), with a material property value, which is associated with a corresponding voxel of the CT data that are to be added,
   wherein in the step of the blending and in the step of the replacement, corresponding spatial coordinates are associated with the corresponding voxel and the particular voxel.

8. The production method according to claim 1, wherein the CT data (B, BM, TM, T, A) comprise at least: one value for a material property; and coordinates for determining the position of a voxel, which is associated with the at least one value for a material property.

9. A computer program product having a computer program, which has software means for carrying out a method according to claim 1 when the computer program is run in an automation system.

10. A production apparatus for producing test X-ray images, wherein the production apparatus comprises:
    an inspection object database for storing produced first CT data (B) of inspection objects;
    a target object database with fourth CT data (T) of target objects; and
    an image projection unit for projecting the fourth CT data of a target object from the target object database into first CT data (B) from the inspection object database in order to produce CT test image data (FTI), wherein the image projection unit is set up to carry out a production method according to claim 1.

11. The production apparatus according to claim 10, wherein the production apparatus has an automation system for carrying out the production method.

12. A central control unit for at least one X-ray inspection unit for nondestructive inspection of an inspection object including a luggage item or other package, having a production apparatus according to claim 9.

13. The central control unit according to claim 12, having at least one display unit for displaying X-ray images of a current inspection object for visual inspection by an operator or for displaying a test X-ray image.

14. An X-ray inspection unit for nondestructive inspection of an inspection object including a luggage item or other package, which has a central control unit according to claim 12 or is operatively and communicatively connected thereto.

15. A luggage or package screening system having at least one X-ray inspection unit and a central control unit according to claim 12.

16. The production method according to claim 4, where q is a value between 0.03 and 0.04.

17. The production method according to claim 4, where q is 0.04.

18. The production method according to claim 10, wherein the material property is at least one of an absorption coefficient, a material density value, and an atomic number.

19. The production method according to claim 10, wherein the coordinates are three-dimensional (3D) coordinates.

20. The central control unit of claim 12, wherein the control unit is connected to the at least one X-ray inspection unit via a communication network.

* * * * *

UNITED STATES PATENT AND TRADEMARK OFFICE
CERTIFICATE OF CORRECTION

| | | |
|---|---|---|
| PATENT NO. | : 11,103,198 B2 | Page 1 of 1 |
| APPLICATION NO. | : 16/484348 | |
| DATED | : August 31, 2021 | |
| INVENTOR(S) | : Durzinsky et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 14 days.

Signed and Sealed this
Seventh Day of February, 2023

Katherine Kelly Vidal
*Director of the United States Patent and Trademark Office*